United States Patent [19]

Morton

[11] Patent Number: 4,461,235
[45] Date of Patent: Jul. 24, 1984

[54] VAPOR PHASE ACTIVATOR PAD FOR A SELF-CONTAINED FINGERPRINTING KIT

[76] Inventor: William P. Morton, 11260 Missouri Ave., Los Angeles, Calif. 90025

[21] Appl. No.: 516,122

[22] Filed: Jul. 20, 1983

[51] Int. Cl.$^3$ ............................................... A61B 5/10
[52] U.S. Cl. ........................................ 118/31.5; 427/1
[58] Field of Search ............................ 118/31.5; 427/1

[56] References Cited

U.S. PATENT DOCUMENTS

| | | | |
|---|---|---|---|
| 4,258,073 | 3/1981 | Payne | 427/1 |
| 4,258,644 | 3/1981 | Goettert et al. | 118/31.5 |
| 4,260,645 | 4/1981 | Kerr et al. | 427/1 |
| 4,297,383 | 10/1981 | Bourdon | 427/1 |
| 4,379,178 | 4/1983 | Meadows et al. | 427/1 |
| 4,381,159 | 4/1983 | Payne | 118/31.5 X |

*Primary Examiner*—James R. Hoffman
*Attorney, Agent, or Firm*—W. Edward Johansen

[57] ABSTRACT

The present invention is a vapor phase activator pad for use in a self-contained fingerprinting kit which includes a portable vapor tank into which the vapor phase activator pad is placed in order to fume an object suspected of containing latent fingerprints, the vapor phase activator pad includes a gauze pad. The gauze pad is chemically treated with a composition which consists of specified chlorinated organic solvents so that when a quantity of alkyl-cyanoacrylate is placed onto the vapor phase activator pad, the vapor phase activator pad generates vapors of the chemical cyanoacrylate. The composition consists of a first component and a second component. The first component is a mixture of two selective chemicals, trichloroethane in the range of 1 to 96 percent and stabilized with methanol in the range of 1 to 10 percent. The second component is a mixture of four selective chemicals, nitroethane and nitromethane in the range of 1 to 5 percent and stabilized with toluene in the range of 1 to 4 percent. The second component also includes an activator which is diethylenetriamine in the range of 1 to 9 percent wherein the composition provides a controlled oxidative vaporization of the quantity of alkyl-cyanoacrylate.

4 Claims, No Drawings

VAPOR PHASE ACTIVATOR PAD FOR A SELF-CONTAINED FINGERPRINTING KIT

BACKGROUND OF THE INVENTION

1. Field of the Invention

The present invention relates to a system for fuming an object suspected of containing latent fingerprints thereon with vapors of the chemical cyanoacrylate and more particularly to a gauze pad which is treated with a composition which includes chlorinated organic solvents and which functions as a base for activating an alkylcyanoacrylate fuming acton in order to generate rapid and prolonged fuming with the vapors.

2. Description of the Prior Art

U.S. Pat. No. 4,297,383, entitled Apparatus and Method for Obtaining Fingerprints, issued to Louis P. Bourdon on Oct. 27, 1981, teaches an apparatus and method for developing latent fingerprints on an object. The apparatus includes a first chamber which contains the object and which closes in order to seal the first chamber air-tight and form a vapor tank and a second chamber which contains a chemical pool and vapors thereof. The apparatus also includes a pump system which pumps vapors from the second chamber into the vapor tank. The method includes the step of pumping the vapors into the vapor tank in order to fume the object with the vapors of the chemical cyanoacrylate and to develop the latent fingerprints on the object being tested inside the vapor tank. U.S. Pat. No. 3,546,003 teaches a similar apparatus and method for obtaining latent fingerprints.

U.S. Pat. No. 4,260,645, entitled Latent Fingerprint Detection, issued to F. Michael Kerr and Alan D. Westland on Apr. 7, 1981, teaches a method of detecting and visualizing a latent fingerprint which includes the step of applying a solution to a suspected locale. The solution includes a volatile organic solvent and selected salts soluble in the volatile organic solvent. The salts include silver perchlorate and silver trifluoroacetate. The non-aqueous solution is preferably applied as a spray and minimizes smudging, "running", warping, and other damage to water-sensitive materials such as inks, dyes and/on cellulosis substrates.

U.S. Pat. No. 4,258,073, entitled Taking of Finger Prints, issued to John M. Payne on Mar. 24, 1981, teaches a method of revealing a fingerprint which includes the steps of charging a surface bearing the fingerprint to a high electric potential and applying a finely divided carbon to the charged surface in order to form a pattern thereon which corresponds to the fingerprint. The method of revealing a fingerprint also includes the steps of either dusting or spraying the finely divided carbon onto the charged surface and applying a transparent protective layer in order to fix the pattern of finely divided carbon in position. Alternatively the finely divided carbon may be in suspension in a dielectric liquid into which the charged surface is introduced.

U.S. Pat. No. 4,381,159, entitled Magnetic Fingerprint Dusting Brush, issued to John M. Payne on Apr. 26, 1983, teaches a magnetic fingerprint dusting brush which includes a handle which incorporates a magnetic portion that projects at one end thereof and a non-magnetic shroud which is assembled with the handle closely to shroud the projecting magnetic portion. The shroud includes an inner blind sleeve for closely shrouding the projecting magnetic portion and an outer sleeve to which a cover is detachably secured. The inner blind sleeve has a first portion of greater cross-section for assembly with the handle and a coaxial second portion of lesser cross-section which is connected to the first portion through a shoulder for closely shrouding the projecting magnetic portion. The magnetic fingerprint dusting brush also includes a cover which is detachably securable to the handle and shroud assembly to form in its secured position an enclosed powder reservoir around the shrouded magnetic portion of the handle. The shroud and the cover assembly constitute a powder cartridge with the handle. The powder reservoir contains a mixture of ferrous and dusting powder.

U.S. Pat. No. 4,379,178, entitled Fingerprinting System, issued to Louis B. Meadows and Arthur S. Diamond on Apr. 5, 1983, teaches a method for forming fingerprint images which includes the steps of prewetting and cleaning the portion of a finger with a cloth impregnated with a detergent solution and applying the distal portion of a finger to a porous pad impregnated with a solution of marking compound. The method for forming fingerprint images also includes the steps of applying the distal portion of the finger to square of a fingerprint card impregnated with an aqueous solution of a polyhydroxy developer, such as a solution of 8-hydroxy-quinoline and propyl gallate containing a high molecular weight dibasic acid, such as azelaic acid and, when the fingerprint image immediately develops, removing traces of the images with a cloth impregnated with a cleaning solution.

U.S. Pat. No. 4,258,644, entitled Depositing Latent Fingerprints and Development Thereof, issued to Edward J. Goettert and George V. D. Tiers on Mar. 31, 1981, teaches a method of depositing and developing a latent fingerprint which includes the steps of making a composition which includes a trimeric aliphatic acid of at least 30 carbon atoms which is substantive to paper fibers, substantially non-volatile, non-hardening, non-toxic and non-hydroscopic and using the composition to apply the fingerprint, which has a latency of several weeks, to a paper substrate. The method of depositing and developing a latent fingerprint also includes the steps of dusting the latent fingerprints in the conventional manner with a suitable toner particles, such as magnetic particles in an oleophilic matrix and developing the latent fingerprint.

SUMMARY OF THE INVENTION

In view of the foregoing factors and conditions which are characteristic of the prior art it is the primary object of the present invention to provide a system for fuming an object suspected of containing latent fingerprints thereon with vapors of the chemical cyanoacrylate.

It is another object of the present invention to provide a gauze pad which is treated with a composition which includes chlorinated organic solvents and which functions as a base for activating an alkyl-cyanoacrylate fuming acton in order to generate rapid and prolonged fuming with the vapors.

It is still another object of the present invention to provide a gauze pad which is treated with a first chemical and second chemical and which generates vapors of the chemical cyanoacrylate for rapid and prolonged fuming for use in a system for fuming an object suspected of containing latent fingerprints.

It is yet another object of the present invention to provide a self-contained fingerprinting kit which incorporates a portable vapor tank and a chemically treated gauze pad for generating vapors of the chemical cyanoacrylate in order to fume an object.

In accordance with the preferred embodiment of the present invention a vapor phase activator pad for use in a self-contained fingerprinting kit is described. The self-contained fingerprinting kit includes a portable vapor tank into which the vapor phase activator pad is placed in order to fume an object suspected of containing latent fingerprints, the vapor phase activator pad includes a gauze pad. The gauze pad is chemically treated with a composition which consists of specified chlorinated organic solvents so that when a quantity of alkyl-cyanoacrylate is placed onto the vapor phase activator pad, the vapor phase activator pad generates vapors of the chemical cyanoacrylate. The composition consists of a first component and a second component. The first component is a mixture of two selective chemicals, trichloroethane in the range of 1 to 96 percent and stabilized with methanol in the range of 1 to 10 percent. The second component is a mixture of four selective chemicals, nitroethane and nitromethane in the range of 1 to 5 percent and stabilized with toluene in the range of 1 to 4 percent. The second component also includes an activator which is diethylenetriamine in the range of 1 to 9 percent wherein the composition provides a controlled oxidative vaporization of the quantity of alkyl-cyanoacrylate.

The features of the present invention which are believed to be novel are set forth with particularity in the appended claims.

Other claims and many of the attendant advantages will be more readily appreciated as the same becomes better understood by reference to the following detailed description and considered in connection with the accompanying drawing in which like reference symbols designate like parts throughout the figures.

DESCRIPTION OF THE PREFERRED EMBODIMENT

In order to best understand the present invention it is necessary to refer to the following description of its preferred embodiment. The present invention is a vapor phase activator pad for use in a self-contained fingerprinting kit which includes a portable vapor tank into which the vapor phase activator pad is placed in order to fume an object suspected of containing latent fingerprints, the vapor phase activator pad includes a gauze pad. The gause pad is chemically treated with a composition which consists of specified chlorinated organic solvents so that when a quantity of alkyl-cyanoacrylate is placed onto the vapor phase activator pad, the vapor phase activator pad generates vapors of the chemical cyanoacrylate. The composition consists of a first component and a second component. The first component is a mixture of two selective chemicals, trichloroethane in the range of 1 to 96 percent and stabilized with methanol in the range of 1 to 10 percent. The second component is a mixture of four selective chemicals, nitroethane and nitromethane in the range of 1 to 5 percent and stabilized with toluene in the range of 1 to 4 percent. The second component also includes an activator which may be selected from a group of organic chemical compounds which includes diethylenetriamine, triethylenetetramine, tetraethlenepentamine, Azamine 11 and Azamine 21 in the range of 1 to 9 percent wherein the composition provides a controlled oxidative vaporization of the quantity of alkyl-cyanoacrylate.

The vapor phase activator pad is placed in a hermetically sealed plastic bag in order to contain the volative composition.

From the foregoing it can be seen that a self-contained fingerprinting kit which incorporates a portable vapor tank and a chemically treated gauze pad for generating vapors of the chemical cyanoacrylate in order to fume an object suspected of containing latent fingerprints has been described.

Accordingly it is intended that the foregoing disclosure and showing shall be considered only as an illustration of the principles of the present invention.

What is claimed is:

1. A vapor phase activator pad for use in a self-contained fingerprinting kit which includes a portable vapor tank into which said vapor phase activator pad is placed in order to fume an object suspected of containing latent fingerprints, said vapor phase activator pad comprising:
   a. a gauze pad;
   b. a composition which consists of specified chlorinated organic solvents wherein said gauze pad is chemically treated with said composition so that when a quantity of alkyl-cyanoacrylate is placed onto said vapor phase activator pad, said vapor phase activator pad generates vapors of the chemical cyanoacrylate.

2. A vapor phase activator pad according to claim 1 wherein said composition consists of:
   a. a first component which is a mixture of two selective chemicals, trichloroethane in the range of 1 to 96 percent and stabilized with methanol in the range of 1 to 10 percent; and
   b. a second component which is a mixture of four selective chemicals, nitroethane and nitromethane in the range of 1 to 5 percent and stabilized with toluene in the range of 1 to 4 percent, said second component also includes an activator which is diethylenetriamine in the range of 1 to 9 percent wherein said composition provides a controlled oxidative vaporization of said quantity of alkyl-cyanoacrylate.

3. A vapor phase activator pad according to claim 1 wherein said composition consists of:
   a. a first component which is a mixture of two selective chemicals, trichloroethane in the range of 1 to 96 percent and stabilized with methanol in the range of 1 to 10 percent; and
   b. a second component which is a mixture of three selective chemicals, nitroethane in the range of 1 to 5 percent and stabilized with toluene in the range of 1 to 4 percent, said second component also includes an activator which is diethylenetriamine in the range of 1 to 9 percent wherein said composition provides a controlled oxidative vaporization of said quantity of alkyl-cyanoacrylate.

4. A vapor phase activator pad according to claim 1 wherein said composition consists of:
   a. a first component which is a mixture of two selective chemicals, trichloroethne in the range of 1 to 96 percent and stabilized with methanol in the range of 1 to 10 percent; and
   b. a second component which is a mixture of three selective chemicals, nitromethane in the range of 1 to 5 percent and stabilized with toluene in the range of 1 to 4 percent, said component also includes an activator which is diethylenetriamine in the range of 1 to 9 percent wherein said composition provides a controlled oxidative vaporization of said quantity pf alkyl-cyanoacrylate.

* * * * *